United States Patent
Katzberg

(10) Patent No.: US 12,167,887 B2
(45) Date of Patent: *Dec. 17, 2024

(54) TRANSORAL ULTRASOUND PROBE

(71) Applicant: Oral Diagnostix, LLC, Green Valley, AZ (US)

(72) Inventor: Richard W. Katzberg, Clinton, SC (US)

(73) Assignee: Oral Diagnostix, LLC, Green Valley, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,912

(22) Filed: Oct. 24, 2023

(65) Prior Publication Data

US 2024/0050146 A1  Feb. 15, 2024

Related U.S. Application Data

(63) Continuation of application No. 17/398,513, filed on Aug. 10, 2021, now Pat. No. 11,839,421, which is a continuation of application No. 16/014,793, filed on Jun. 21, 2018, now Pat. No. 11,116,568.

(60) Provisional application No. 62/524,196, filed on Jun. 23, 2017.

(51) Int. Cl.
*A61B 18/14* (2006.01)
*A61B 8/00* (2006.01)
*A61B 8/08* (2006.01)
*A61B 8/12* (2006.01)

(52) U.S. Cl.
CPC ........ *A61B 18/1477* (2013.01); *A61B 8/0875* (2013.01); *A61B 8/12* (2013.01); *A61B 8/4209* (2013.01); *A61B 8/4281* (2013.01); *A61B 8/4444* (2013.01)

(58) Field of Classification Search
CPC ..... A61B 18/1477; A61B 8/0875; A61B 8/12; A61B 8/4209; A61B 8/4281; A61B 8/4444; A61B 8/14; A61B 8/4455; A61B 8/445; A61B 8/56; A61B 8/4483; A61C 9/0086

See application file for complete search history.

(56) References Cited

U.S. PATENT DOCUMENTS

| | | | |
|---|---|---|---|
| 5,368,478 A | 11/1994 | Andreiko et al. | |
| 5,400,790 A * | 3/1995 | Pohan | G10K 11/355 600/446 |
| 5,456,258 A * | 10/1995 | Kondo | A61B 8/445 600/463 |
| 5,690,113 A | 11/1997 | Sliwa, Jr. et al. | |
| 5,755,571 A | 5/1998 | Companion | |

(Continued)

FOREIGN PATENT DOCUMENTS

| | | |
|---|---|---|
| CN | 202104898 U | 1/2012 |
| CN | 104968281 A | 10/2015 |

(Continued)

OTHER PUBLICATIONS

Decision to Grant dated Jan. 16, 2024 issued in JP Application No. 2022-199097.

(Continued)

*Primary Examiner* — Peter Luong
(74) *Attorney, Agent, or Firm* — Blank Rome LLP

(57) ABSTRACT

A transoral ultrasound probe for imaging a temporomandibular joint and a method of imaging a temporomandibular joint using a transoral probe.

19 Claims, 2 Drawing Sheets

(56) References Cited

U.S. PATENT DOCUMENTS

| | | | |
|---|---|---|---|
| 5,779,639 | A | 7/1998 | Yeung |
| 5,931,788 | A | 8/1999 | Keen et al. |
| 6,050,821 | A | 4/2000 | Klaassen et al. |
| 6,102,704 | A | 8/2000 | Eibofner et al. |
| 6,248,074 | B1 | 6/2001 | Ohno et al. |
| 6,402,707 | B1 | 6/2002 | Ernst |
| 6,638,219 | B1 | 10/2003 | Asch et al. |
| 7,296,996 | B2 | 11/2007 | Sachdeva et al. |
| 7,477,925 | B2 | 1/2009 | Lockhart et al. |
| 8,043,091 | B2 | 10/2011 | Schmitt |
| 8,226,407 | B2 | 7/2012 | Hanewinkel et al. |
| 8,366,442 | B2 | 2/2013 | Schmitt |
| 8,366,626 | B2 | 2/2013 | Kafai El-Khorassani |
| 8,457,772 | B2 | 6/2013 | Glasson et al. |
| 8,550,816 | B2 | 10/2013 | Hanewinkel et al. |
| 9,877,700 | B1 | 1/2018 | Asch |
| 2002/0061495 | A1 | 5/2002 | Mault |
| 2004/0143186 | A1 | 7/2004 | Anisimov et al. |
| 2005/0070782 | A1 | 3/2005 | Brodkin |
| 2006/0029904 | A1 | 2/2006 | Rose et al. |
| 2006/0240378 | A1 | 10/2006 | Weinstein et al. |
| 2007/0037125 | A1 | 2/2007 | Maev et al. |
| 2008/0124680 | A1 | 5/2008 | Brandhorst et al. |
| 2009/0263759 | A1 | 10/2009 | Van Herpern |
| 2009/0281433 | A1 | 11/2009 | Saadat et al. |
| 2009/0306506 | A1 | 12/2009 | Heger et al. |
| 2010/0124732 | A1 | 5/2010 | Ariff |
| 2010/0191123 | A1 | 7/2010 | Tsung |
| 2010/0198069 | A1 | 8/2010 | Kafai El-Khorassani |
| 2010/0239996 | A1 | 9/2010 | Ertl |
| 2010/0279248 | A1 | 11/2010 | Mourad et al. |
| 2011/0008756 | A1 | 1/2011 | Brandhorst et al. |
| 2011/0104632 | A1 | 5/2011 | Colby |
| 2011/0200960 | A1 | 8/2011 | Colby |
| 2011/0200961 | A1 | 8/2011 | Colby |
| 2012/0136626 | A1 | 5/2012 | Mucha |
| 2013/0060144 | A1 | 3/2013 | Culjat et al. |
| 2013/0109932 | A1 | 5/2013 | Saadat et al. |
| 2013/0122458 | A1 | 5/2013 | Pan et al. |
| 2013/0171580 | A1 | 7/2013 | Van Lierde et al. |
| 2013/0225995 | A1 | 8/2013 | Hashiguchi |
| 2015/0374331 | A1 | 12/2015 | Cho et al. |
| 2018/0140275 | A1 | 5/2018 | Yoshimine |

FOREIGN PATENT DOCUMENTS

| | | |
|---|---|---|
| CN | 206166941 U | 5/2017 |
| DE | 10 2015011 388 A1 | 3/2017 |
| EP | 3641655 A1 | 4/2020 |
| WO | WO 2018237162 A1 | 12/2018 |

OTHER PUBLICATIONS

Schiffman E. et al. "Diagnostic Criteria for Temporomandibular Disorders (DC/TMD) for Clinical and Research Applications: Recommendations of the International RDC/TMD Consortium Network and Orofacial Pain Special Interest Group," J Oral Facial Pain Headache 2014; 28: 6-27.

Katzberg Richard W. et al., "Pilot Study to 1-15 Show the Feasibility of High-Resolution Sagittal Ultrasound Imaging of the Temporomandibular Joint", Journal of Oral and Maxillofacial Surgery, Saunders, Philadelphia, PA, US, vol. 75, No. 6, Dec. 12, 2016, pp. 1151-1162.

Salmon Benjamin et al. "Intraoral Ultrasonography: Development of a Specific High-Frequency Probe and Clinical Pilot Study", Clinical Oral Investigations, Sprinter, Berlin, DE, vol. 16, No. 2, Mar. 5, 2011, pp. 643-649.

Yoshida et al., "Intraoral Ultrasonic Scanning as a Diagnostic Aid", Journal of Cranio-Maxillo-Facial Surgery, Churchill Livingstone, GB, vol. 15. 15, Jan. 1, 1987, pp. 306-311.

Schiffman E, et al. Effects of four treatment strategies for temporomandibular joint closed lock. Int. J Oral Maxiillofac Surt., 2014; 43(2):217-226.

Detamore MS, Athanasiou KA. A call to action for bioengineers and dental professionals: Directives for the future of TMJ bioengineering. Annals of Biomedical Engineering 2007; 35:1301-1311.

Ahmad M, Hollender L, Anderson Q et al. Research diagnostic criteria for temporomandibular disorders (RDC/TMD): development of image analysis criteria and examiner reliability for image analysis. Oral Surg Oral Med Oral Pathol Oral Radiol Endod 2009; 107:844-860.

Bushberg JT, Seibert JA, Leidholdt EM Jr, Boone JM. The Essential Physics of Medical Imaging. Chapter 12 Ultrasound pp. 367-416. Williams & Wilkins, Baltimore MD 1994.

Westesson P-L. Are high-resolution ultrasonic signs of disc displacement valid? J Oral Maxillofac Surg 2002; 60:628-629.

Katzberg RW. Is ultrasonography of the TMJ ready for prime time? Is there a "window" of opportunity? J Oral Maxillofac Surg 2012; 70:1310-1315.

Dupuy-Bonafe I, Picot M-C, Maldanado IL, et al. Internal derangement of the temporomandibular joint: is there still a place for ultrasound? Oral Surg Oral Med Oral Pathol Oral Radiol 2012; 113:832-840.

Katzberg RW, Dolwick MF, Bales DJ, Helms CA. Arthrotomography of the temporomandibular joint: new technique and preliminary observations. Am J Roentgenol 1979; 161:100-105.

Westesson P-L, Omnell KA, Rohlin M. Double-contrast tomography of the temporomandibular joint: a new technique based on autopsy specimen examinations. Acta Radiol (Diag) (Stockholm) 1980; 21:777-784.

Dolwick MF. Sagittal anatomy of the temporomandibular joint spaces: normal and abnormal findings. J Oral Maxillofac Surg 1983; 41:86-88.

Manzione JV, Katzberg RW, Brodsky GL et al. Internal derangements of the temporomandibular joint: diagnosis by direct sagittal computed tomography. Radiology 1984; 150:111-115.

Manco LG, Messing SG, Busino LJ, et al. Internal derangements of the temporomandibular joint evaluated with direct sagittal CT: a prospective study. Radiology 1985; 157:407-412.

Harms SE, Wilk RM, Wolford LM et al. The Temporomandibular joint: magnetic resonance using surface coils. Radiology 1985; 157:133-136.

Katzberg RW, Bessette RW, Tallents RH. Normal and abnormal temporomandibular joint: MR imaging with surface coil. Radiology 1986; 158:183-189.

Westesson P-L, Katzberg RW, Tallents RH et al. CT and MR of the temporomandibular joint. Am J Roentgenol 1987; 148:1165-1171.

Katzberg RW. State of the Art: Temporomandibular joint imaging. Radiology 1989; 170:297-307.

Palacios E, Valvassori GE, Shannon M, Reed CF. Magnetic Resonance of the temporomandibular joint. Clinical considerations, Radiography, Management. 1990 Thieme Medical Publishers, Inc. New York (Chapter 3, Bell KA. Computed Tomography of the Temporomandibular Joint, pp. 28-39.

Palacios E, Valvassori GE, Shannon M, Reed CF. Magnetic Resonance of the temporomandibular joint. Clinical considerations, Radiography, Management. 1990 Thieme Medical Publishers, Inc. New York Chapter 5, Shannon M, Palacios E, Valvassori GE, Reed CF. MR of the Normal Temporomandibular Joint, pp. 48-63).

Som PM, Bergeron RT, editors. Head and Neck Imaging 2nd Edition 1991, Moxby Year Book, St. Louis, Missouri. (Chapter 4, Temporomandibular Joint Imaging. Katzberg RW, Westesson P-L pp. 349-378).

Katzberg RW, Westesson P-L. Diagnosis of the Temporomandibular Joint. W.B. Saunders Company, Philadelphia, PA 1993. (Chapter 5 Magnetic Resonance Imaging, pp. 167-222; Chapter 6 Miscellaneous Modalities: Computed Tomography. Single Photon Emission Computed Tomography, and Sound Analysis, pp. 223-260).

Emshoff R, Jank S, Rudisch A, et al. Are high-resolution ultrasonic signs of disc displacement valid. J Oral Maxillofac Surg. 2002; 60:623-628.

Melis M, Secci, Coneviz C. Use of ultrasonography for the diagnosis of temporomandibular disorders: A review. Am J Dent 2007; 20:73-78.

(56) References Cited

OTHER PUBLICATIONS

Li C, Su N, Yang X, et al. Ultrasonography for detection of disc displacement of temporomandibular joint: a systematic review and meta-analysis. J Oral Maxillofac Surg. 2012; 70:1300-1309.

Landes CA, Goral WA, Sader R, Mack MG. Three-dimensional versus two-dimensional sonography of the temporomandibular joint in comparison to MRI. Eur J Radiol 2007; 61:235-244.

Landis JR, Koch GG. The measurement of observer agreement for categorical data. Biometrics 1977; 33:159-174.

Fleiss JL, Levin B Paik MC. Statistical methods for rates and proportions. 3rd edition. Hoboken (NJ): John Wiley & Sons; 2003:598-626.

Kundu H, Basavaraj P, Kote S, et al. Assessment of TMJ disorders using ultrasonography as a diagnostic tool: a review. J Clin Diagn Res. 2013; 7:3116-3120.

Communication Under Rule 71 (3) EPC dated Sep. 27, 2023 issued in corresponding EP Aoolication No. 18 820 272.5.

Office Action issued in corresponding Canadian Patent Application No. 3,066,884 dated Oct. 14, 2021.

Chinese Office Action dated Jan. 28, 2022 from corresponding CN Application No. 201880042189.7.

\* cited by examiner

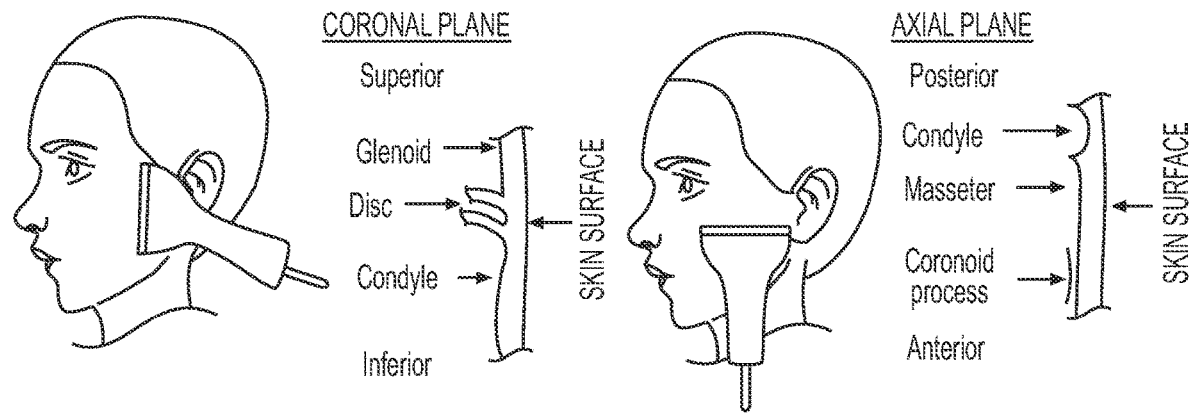
FIG. 1
*PRIOR ART*
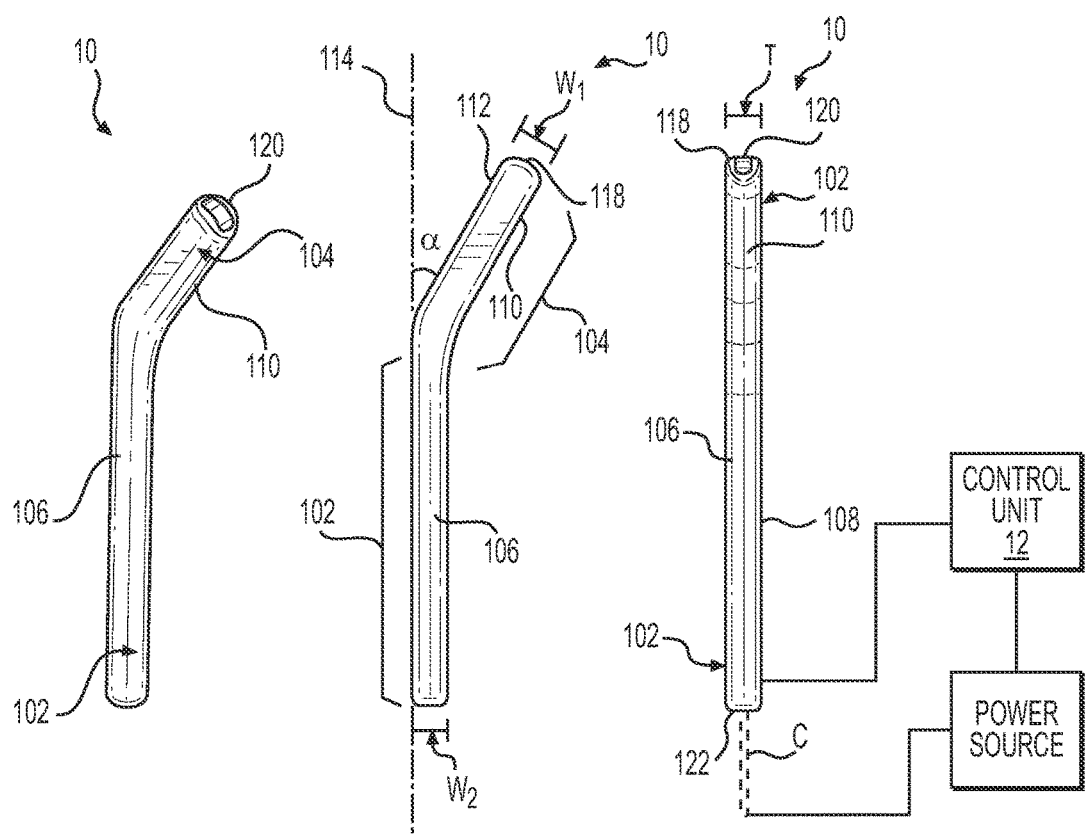
FIG. 2A  FIG. 2B  FIG. 2C

TRANSORAL ULTRASOUND PROBE

RELATED APPLICATIONS

The present application is a continuation of U.S. application Ser. No. 17/398,513, entitled Transoral Ultrasound Probe and Method of Use, filed on Aug. 10, 2021, which is a continuation of U.S. application Ser. No. 16/014,793, entitled Transoral Ultrasound Probe and Method of Use, filed on Jun. 21, 2018, now U.S. Pat. No. 11,116,568, which claims priority to U.S. provisional application No. 62/524,196, filed Jun. 23, 2017, the entire disclosure of each of which is incorporated herein by reference.

FIELD OF THE INVENTION

The present invention relates to a transoral probe for ultrasound imaging of the jaw, namely the temporomandibular joint.

BACKGROUND

Temporomandibular disorders (TMD) are a significant public health problem that represents a group of potentially debilitating conditions affecting approximately 5% to 12% of the population in the U.S. TMD is the second most common musculoskeletal condition (after chronic low back pain) that is associated with pain and disability and is often the result of disc displacement and the resulting mechanical temporomandibular joint (TMJ) dysfunction. Pain-related TMD can impact an individual's daily activities, psychosocial function, and quality of life. Research regarding disc displacement has indicated that the clinical approaches for assessing disc displacement can lead to diagnoses that exhibit sensitivities as low as 0.34-0.54 Volts p-p. Consequently, improved clinical diagnosis, treatment decision-making in specific presentations, and confirmation of the diagnosis of disc displacement, requires imaging.

Current TMJ imaging technologies include panoramic radiographs, cone beam CT (CBCT) for hard tissues only, and magnetic resonance imaging (MRI). There are several barriers to the widespread use of these technologies and effectiveness for TMD diagnosis, such as the medical risk of exposure to ionizing radiation with panoramic radiographs and CBCT, high cost of both CBCT and MRI, limited accessibility of MRI systems that are located in hospitals and medical imaging laboratories, and patient-related claustrophobic concerns and the consequent management requirements for anxiolytics. Arthrography has also been previously used for imaging but was abandoned due to its invasive nature.

Prior attempts at developing ultrasound imaging of the TMJ have been suboptimal due to the utilization of large-sized imaging probes that are constrained to imaging approaches of only the axial and coronal anatomical planes because the images can only be acquired externally from the side of the patient's face. Bone barriers restrict sound penetration to only the superficial aspect of the entire TMJ soft tissue anatomy. Even if ultrasound energy had the penetrating ability to image the entire axial and coronal TMJ anatomy, these two anatomical planes of imaging are not adequate to depict disc displacement. Research has shown that the external imaging approach, as shown in FIG. 1, achieved only a 22.8% specificity for disc displacement in the closed-mouth position and zero specificity for disc displacement in the opened—mouth position.

FIG. 1 illustrates such suboptimal ultrasound imaging approached externally with large probes. The external facial approach has not gained clinical acceptance because: 1) the sound penetration is severely limited by the markedly contoured anatomy of the bones of the condyle, tubercle and zygomatic arch of the TMJ; and 2) of being limited to the depiction of only the axial (transverse) and coronal (longitudinal) planes of imaging. The external bone barriers restrict sound penetration to only the superficial aspects of the TMJ anatomy. Extensive literature and extensive clinical experiences derived from TMJ arthrotomography, CT and MRI, have proven that the sagittal plane of imaging is preferred for the effective and accurate depiction of TMJ disc displacement.

Therefore, there is a need for imaging modality that can accurately depict dynamic TMJ function as an integral characteristic of routine medical ultrasound imaging.

SUMMARY

A transoral ultrasound probe for imaging a temporomandibular joint, comprising a handle section that has a longitudinal axis, the handle section being configured for connection to a power source; and an intraoral section that has a cephalad angulation such that the intraoral section is positioned at an operative angle with respect to the longitudinal axis of the handle section, and the intraoral section is configured to emit and receive sound waves. The operative angle of the intraoral section is preferably an acute angle.

In one embodiment, the operative angle is less than 45 degrees and/or is about 30 degrees. In a certain embodiment, the handle section has a longitudinal length and the intraoral section has a length that is about one-third shorter than the longitudinal length of the handle section; the handle section has a first width and the intraoral section has a second width, and the second width is greater than the first width; the handle section and the intraoral section have substantially the same thickness and the thickness is less than or equal to the first width; the handle and intraoral sections define substantially flat side surfaces and the thickness extends between the side surfaces; a distal end of the intraoral section is rounded; the intraoral section includes a transducer aperture at a distal end thereof configured to emit and receive the sound waves; the handle section is connected to the power source via a power cable or the power source is at least one battery connected to the handle section; and/or the power source is either coupled to or is part of a control unit.

A transoral ultrasound probe that comprises a handle section that has a longitudinal axis, and the handle section is configured for connection to or receipt of a power source. An intraoral section that has a cephalad angulation such that the intraoral section is positioned at an operative angle with respect to the longitudinal axis of the handle section. The intraoral section is configured to emit and receive sound waves. The handle section and the intraoral section may have substantially the same thickness.

A transoral ultrasound probe that comprises a handle section that has a longitudinal axis, and the handle section is configured for connection to or receipt of a power source. An intraoral section that has an angulation such that the intraoral section is positioned at an operative angle with respect to the longitudinal axis of the handle section. The intraoral section is configured to emit and receive sound waves. The handle section has a first width and the intraoral section has a second width, and the second width may be greater than the first width. The handle section and the intraoral section may have substantially the same thickness and the thickness may be less than or equal to the first width.

In one embodiment, the probe has a first side surface and a second side surface opposite the first side surface, and each of the first and second side surfaces is continuous and substantially flat between opposite ends of the probe. In another embodiment, a thickness of the handle section is the same as a thickness of the intraoral section, thereby defining a continuous thickness between opposite ends of the probe.

A method of imaging a temporomandibular joint using a transoral probe that has a handle section and an intraoral section with a cephalad angulation, that comprises the steps of holding the handle section of the transoral probe; inserting the intraoral section of the transoral probe into a patient's mouth in a recess between the cheek and gum such that a transducer aperture of the intraoral section generally faces the temporomandibular joint; and emitting and receiving sound waves via the transducer aperture on the intraoral section of the transoral probe thereby producing images of the temporomandibular joint in at least the sagittal anatomical plane.

In one embodiment of the method, the step of emitting and receiving sound waves produces images of the temporomandibular joint in all anatomical planes, including the axial, coronal, and sagittal planes. In other embodiments, the method further comprises the step of controlling the amplitude, frequency, and duration of the sound waves emitted from the transducer aperture of the transoral probe; and/or the step of connecting the transoral probe to a power source. In certain embodiments of the method, the intraoral section of the transoral probe is positioned at an operative angle with respect to a longitudinal axis of the handle section, and the operative angle is an acute angle; the operative angle of the intraoral section is about 30 degrees; the handle and intraoral sections define substantially flat side surfaces and a thickness that extends between the side surfaces; the handle section has a first width and the intraoral section has a second width that is larger than the first width; and/or a distal end of the intraoral section of the transoral probe is rounded.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a diagrammatic view of a prior art method of imaging the temporomandibular joint;

FIGS. 2A thru 2C are perspective and elevational views of a transoral probe according to an exemplary embodiment of the present invention;

DETAILED DESCRIPTION

Figure 3A:
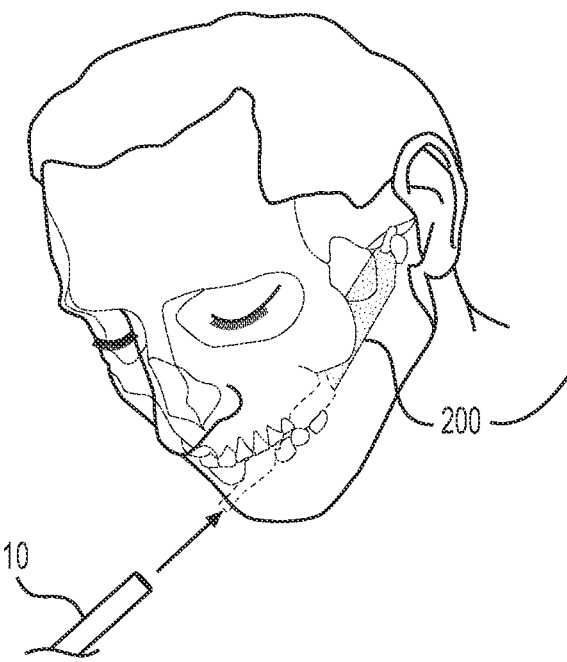
FIGS. 3A thru 3C are diagrammatic views of an exemplary probe orientation and window of imaging into the temporomandibular joint inside of a patient's mouth in accordance with the present invention.

The present invention generally relates to a transoral ultrasound probe 10 and use thereof for imaging inside of a patient's mouth, such as the temporomandibular joint, for diagnosis and treatment of disc displacement disorders. The present invention preferably provides transoral sagittal high resolution dynamic ultrasound as an effective imaging modality to depict temporomandibular joint (TMJ) structure and function. The present invention may be an imaging tool that can detect TMJ disc displacement, assess the onset and progression of disease, and facilitate longitudinal diagnostics to monitor treatment outcomes. The present invention, among other things, advances imaging of TMJ disc displacement to complement the medical history and clinical examination of the patient; provides dynamic TMJ imaging for clinical research and improved imaging capabilities for practicing clinicians in the diagnosis and treatment of TMJ disorders; permits multidimensional joint visualization, particularly useful for routine screening of patients with joint dysfunction; provides images that clearly show the structure of the disc or as a part of the joint capsule or joint effusion; and is ergonomically designed for optimal patient comfort.

TMJ imaging in the clinical setting that is achieved with the transoral ultrasound imaging of the present invention, may be used for screening protocols to establish the presence or absence and severity of disc displacement in TMD patients. Other advantages of the present invention include that it provides non-invasive procedure; there is no ionizing radiation risk; it is capable of 3-D and 4-D imaging of joint function and mechanics; it is accessible and has ease of portability; it is interactive, point-to-care clinical adjunct; and it has a low expense.

Ultrasound imaging is a highly sophisticated medical technology that eliminates and minimizes many of the negatives currently found in TMJ diagnostics. A benefit of the present invention is that ultrasound imaging of TMD will be more readily accessible and have widespread utilization for expanded clinical diagnosis, screening for asymptomatic disease, and research.

The transoral probe 10 of the present invention is designed to acquire ultrasound images of the TMJ via a transoral soft tissue window 200 that depicts the anatomic sagittal plane and is of adequate imaging depth to encompass the entire joint anatomy. The probe 10 of the present invention preferably provides transoral sagittal imaging for impacting this field of research and for point-to-care clinical diagnostics.

The ultrasound probe (or transducer) 10 produces sound waves that bounce off body tissues and make echoes, and also receives the echoes and sends them to a control unit or computer 12 that uses them to create an image or sonogram. The probe 10 is configured to be connected to a power source 14, which may be separate from or part of the control unit 12. The control unit 12 does the calculations and can display and/or print the processed images. In one embodiment, the probe 10 is connected to the power source 14 via a power cable C. Alternatively, the power source 14 may be one or more batteries connected to or received in the probe 10. The control unit 12 may also include pulse control for changing the amplitude, frequency and duration of the sound waves emitted from the probe 10.

The probe 10 is designed for acoustic, mechanical and electrical optimization thereof. The probe 10 may have, for example, about an 8-10 MHz center frequency-wide band (minimum 70%+bandwidth), 32 elements, about 0.3 mm pitch, and about 3.5 mm elevation. The acoustic design of probe 10 may integrate a piezo-composite, for example, with matching layer and backing components optimized for the high resolution for a shallow depth range (e.g. 40-45 mm). The electrical design of the probe 10 may be composed of specialized circuitry to allow construction of the smallest probe size possible. The probe cable exit 122 may be reduced to a circumference as small as possible.

As seen in FIGS. 2A-2C, the transoral probe 10 generally includes a handle section 102 configured to facilitate gripping and manipulation of the probe 10 and an intraoral section 104 configured for insertion into the patient's mouth for ultrasound imaging of the temporomandibular joint. The probe 10 preferably has an ergonomic configuration for patient comfort when the probe 10 is inserted into the patient's mouth. The probe 10 may be ergonomically optimized particularly to fit inside the mouth between the cheek and gum of the soft tissue recess of the posterior maxillary region. The ergonomic configuration of the probe 10 may include substantially flat side surfaces 106 and 108 with opposing generally rounded margins 110 and 112 extending between the side surfaces 106 and 108. In a preferred embodiment, the thickness T of the probe 10 at the margins 110 and 112 is relatively thin, thereby giving the probe 10 a generally flat shape (particularly as compared to the rounded configuration of traditional probes) similar to a spatula.

The ergonomic configuration of the probe 10 is also preferably compact and not bulky or rectangular with squared off edges, like in some conventional probes. The distal end 118 of the intraoral section 104 may be rounded for additional patient comfort. The length of the intraoral section 104 is preferably shorter than the length of the handle section 102. For example, the intraoral section 104 may be about one-third shorter than the handle section 102. In one embodiment, the intraoral section 104 is about 1.88 inches or about 4.5 cm long and the handle section 102 is about 3.77 inches or about 9.5 cm long for a total length of the probe 10 being about 5.66 inches or about 14 cm. The width $W_1$ of the intraoral section 104 is preferably greater or larger than the width $W_2$ of the handle section 102. The width $W_1$ of the intraoral section 104 may be, for example, about 0.45 inches or about 1.1 cm. The thickness T of the probe 10 is preferably the same at both the handle and intraoral sections 102 and 104 and is preferably the same as or less than the width $W_2$ of the handle section 102. The thickness T may be, for example, about 0.35 inches or about 0.9 cm. The ergonomic and compact design of the probe 10 also allows unrestricted movement of the patient's jaw while imaging the same, thereby producing more accurate images of the TMJ movement and also adding to the patient's comfort.

The intraoral section 104 has a cephalad angulation (also known as toward-the-head) such that it is positioned at an operative angle α with respect to a longitudinal axis 114 of the handle section 102 for optimal imaging of the temporomandibular joint and patient comfort when the intraoral section 104 is inserted into the patient's mouth. The operative angle α is preferably less than 90 degrees, more preferably less than 45 degrees, and most preferably about 30 degrees. The intraoral section 104 is configured to emit and receive sound waves via a transducer aperture 120. In a preferred embodiment, the transducer aperture 120 is located at or near the distal end 118 of the intraoral section 104, as best seen in FIGS. 2A and 2C.

Ultrasound imaging according to the present invention may be performed by using a pulse-echo technique, for example, that sends and receives sound waves/energy via the intraoral section 104 and aperture 120. The transoral probe 10 converts electrical energy into a brief pulse of high-frequency sound energy that is transmitted into the patient's tissue. The probe 10 then becomes a receiver, detecting echoes of sound energy reflected from the tissue. Real-time images of moving patient tissues may be produced and displayed via control unit 12 depicting TMJ condyle, disc and muscle movement. In accordance with the present invention, images may be produced in any anatomical (hypothetical) plane, i.e. the axial (or horizontal) plane, the coronal (or vertical) plane, and the sagittal (or median) plane. The axial anatomical plane divides the body into cranial and caudal (head and feet) portions; the coronal anatomical plane divides the body into dorsal and ventral (back and front) portions; and the sagittal anatomical plane divides the body into left and right portions. The transoral probe 10 is designed to allow for images of the TMJ in the sagittal plane, in addition to the axial and coronal planes, which provides the most effective and accurate depiction of the TMJ, including the TMJ disc, condyle, and fossa (and movement thereof).

Figure 3B:
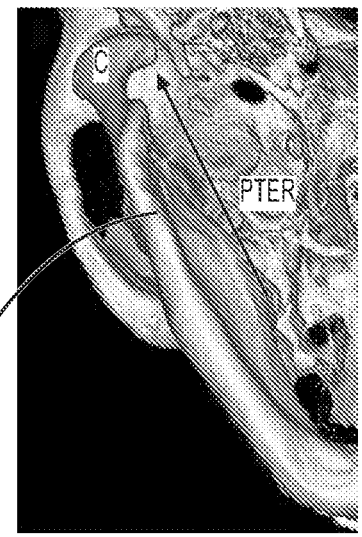
Figure 3C:
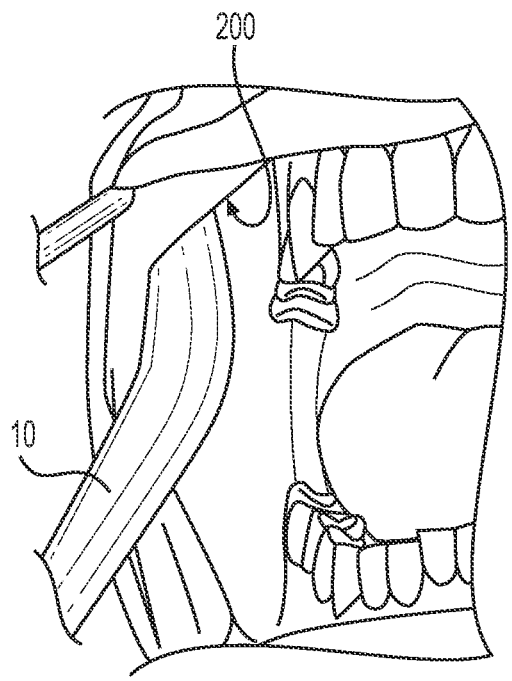

Optimal visualization of the TMJ may be performed through a transoral window (between the cheek and gum) 200 that is devoid of bone to allow adequate sound transmission. FIGS. 3A-3C are diagrammatic views of a preferred orientation of the transoral probe 10 of the present invention, showing how the probe 10 is to be positioned in the window 200 between the cheek and gum of the upper maxillary arch to acquire sagittal ultrasound images of the condyle and disc of the temporomandibular joint therethrough without bone hindrance.

A method of imaging a temporomandibular joint according to the present invention using the transoral probe 10 generally comprises the steps of, once connected to a power source, holding and manipulating the handle section 102 of the transoral probe 10 and inserting the intraoral section 104 into a patient's mouth in the window 200 between the cheek and gum such that the transducer aperture 120 thereof generally faces the temporomandibular joint. Once properly inserted and positioned in the patient's mouth, the probe 10 is activated to emit and receive sound waves via the transducer aperture 120, thereby producing images (via software and control unit 12) of the temporomandibular joint in at least the sagittal anatomical plane and preferably in all of the anatomical planes, i.e. the axial, coronal, and sagittal planes. The amplitude, frequency, and duration of the sound waves emitted from the transducer aperture 120 of the transoral probe 10 may be controlled and adjusted by the control unit 12.

Figure 4:
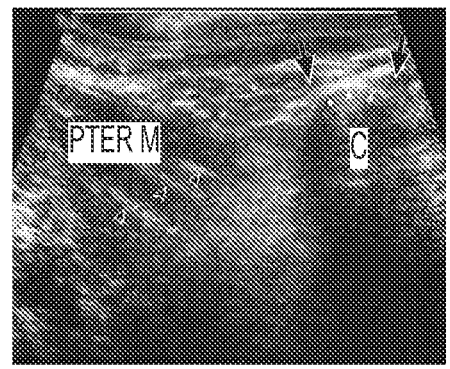
FIG. 4 is an exemplary sonogram image of the temporomandibular joint produced in accordance with the present invention and method.

In unblinded preliminary observations, the present invention provided the first TMJ images acquired by sagittal transoral sonography. The condyle and its subcondylar surface, as seen in FIG. 4, were visible in all subject joints. The condyle (C), which is the rounded protuberance at the end of the bone for articulation with another bone, is vertically oriented and hypoechoic; whereas, the subcondylar surface is arc-shaped and echogenic, having a cap-like appearance (small arrowheads in FIG. 4). The condyle is also identifiable by its translational and rotational motion with jaw opening and closing.

While particular embodiments have been chosen to illustrate the invention, it will be understood by those skilled in the art that various changes and modifications can be made therein without departing from the scope of the invention as defined in the appended claims.

What is claimed is:

1. A transoral ultrasound probe for imaging a temporomandibular joint, comprising:
   a handle section having a longitudinal axis and a first end, the handle section being configured for connection to a power source;
   an intraoral section that is configured to be received in a patient's mouth and having a cephalad angulation such that the intraoral section is positioned at an operative angle with respect to the longitudinal axis of the handle section, the intraoral section being configured to emit and receive sound waves, wherein the operative angle of the intraoral section is an acute angle, the intraoral section having a second end opposite the first end of the handle section; and a first side surface and a second side surface opposite the first side surface, each of the first and second side surfaces being continuous and substantially flat between the opposite first and second ends.

2. The transoral ultrasound probe of claim 1, wherein the handle section has a first width and the intraoral section has a second width, and the second width is greater than the first width.

3. The transoral ultrasound probe of claim 1, wherein the operative angle is about 30 degrees.

4. The transoral ultrasound probe of claim 1, wherein a thickness of the handle section is the same as a thickness of the intraoral section, thereby defining a continuous thickness between the opposite ends of the probe.

5. The transoral ultrasound probe of claim 1, wherein a distal end of the intraoral section is rounded.

6. The transoral ultrasound probe of claim 5, wherein the intraoral section includes a transducer aperture at a distal end thereof configured to emit and receive the sound waves.

7. The transoral ultrasound probe of claim 1, wherein the handle section is connected to the power source via a power cable or the power source is at least one battery connected to the handle section.

8. The transoral ultrasound probe of claim 7, wherein the power source is either coupled to or is part of a control unit.

9. A transoral ultrasound probe, comprising:

a handle section having a longitudinal axis and a first end, the handle section being configured for connection to or receipt of a power source; and an intraoral section that is configured to be received in a patient's mouth and having a cephalad angulation such that the intraoral section is positioned at an operative angle with respect to the longitudinal axis of the handle section, the intraoral section being configured to emit and receive sound waves, and the intraoral section having a second end opposite the first end of the handle section, wherein a thickness of the handle section is the same as a thickness of the intraoral section, thereby defining a continuous thickness between the opposite first and second ends.

10. The transoral ultrasound probe of claim 9, wherein the handle and intraoral sections define substantially flat side surfaces and the thickness extends between the side surfaces.

11. The transoral ultrasound probe of claim 9, wherein a distal end of the intraoral section is rounded and includes a transducer aperture configured to emit and receive the sound waves.

12. The transoral ultrasound probe of claim 9, wherein the handle section is connected to the power source via a power cable or the power source is at least one battery connected to the handle section.

13. The transoral ultrasound probe of claim 9, wherein the operative angle is about 30 degrees.

14. A transoral ultrasound probe, comprising:

a handle section having a longitudinal axis, the handle section being configured for connection to or receipt of a power source; and an intraoral section that is configured to be received in a patient's mouth, the intraoral section having an angulation such that the intraoral section is positioned at an operative angle with respect to the longitudinal axis of the handle section, the intraoral section being configured to emit and receive sound waves, wherein the handle section has a first width and the intraoral section has a second width, and the second width is greater than the first width, and wherein the first width is a largest width of the handle section.

15. The transoral ultrasound probe of claim 14, wherein a thickness of the handle section is the same as a thickness of the intraoral section, thereby defining a continuous thickness between opposite ends of the probe.

16. The transoral ultrasound probe of claim 15, wherein the handle section has a longitudinal length and the intraoral section has a length that is about one-third shorter than the longitudinal length of the handle section.

17. The transoral ultrasound probe of claim 16, wherein the operative angle is about 30 degrees.

18. The transoral ultrasound probe of claim 17, wherein a distal end of the intraoral section is rounded and includes a transducer aperture configured to emit and receive the sound waves.

19. The transoral ultrasound probe of claim 18, wherein the handle section is connected to the power source via a power cable or the power source is at least one battery connected to the handle section.

\* \* \* \* \*